United States Patent [19]

Aoki et al.

[11] Patent Number: 5,056,928
[45] Date of Patent: Oct. 15, 1991

[54] METHOD AND APPARATUS FOR MEASURING A CHANGE IN STATE OF A SUBJECT FLUID

[75] Inventors: Kazuichi Aoki, Moroyama; Yukihiro Saiki, Tsurugashima; Katushtoshi Tanno, Sakato; Yasuhiko Shiinoki, Tokyo; Tomoshige Hori, Kitamoto; Kensuke Itoh, Kodaira; Tetsuo Nakamura, Iruma; Osato Miyawaki, Asaka, all of Japan

[73] Assignee: Snow Brand Milk Products Co., Ltd., Hokkaido, Japan

[21] Appl. No.: 577,760

[22] Filed: Sep. 5, 1990

[30] Foreign Application Priority Data

Sep. 12, 1989 [JP] Japan ............................. 1-106768[U]
Sep. 28, 1989 [JP] Japan ............................. 1-113618[U]
Jan. 24, 1990 [JP] Japan ................................. 2-5347[U]

[51] Int. Cl.$^5$ ............................................. G01N 25/02
[52] U.S. Cl. ........................................ 374/16; 374/163
[58] Field of Search ............... 374/16, 25, 27, 28, 374/45, 163; 73/204.27, 308

[56] References Cited

U.S. PATENT DOCUMENTS

| | | | |
|---|---|---|---|
| 2,349,482 | 5/1944 | Welty, Jr. | 374/16 |
| 2,595,386 | 5/1952 | Kagola | 374/16 |
| 3,150,515 | 9/1964 | Malina | 374/16 |
| 3,263,487 | 8/1966 | Fiske, Jr. | 374/16 |
| 3,447,358 | 6/1969 | Crespin et al. | 374/16 |
| 4,889,434 | 12/1989 | Sollich | 374/16 |
| 4,925,314 | 5/1990 | Clandy et al. | 374/16 |
| 4,971,451 | 11/1990 | Hori et al. | 374/16 |

FOREIGN PATENT DOCUMENTS

| | | | |
|---|---|---|---|
| 0474285 | 6/1951 | Canada | 374/16 |
| 0074415 | 3/1983 | European Pat. Off. | 374/16 |
| 0223742 | 5/1987 | European Pat. Off. | 374/16 |
| 3111160 | 9/1982 | Fed. Rep. of Germany | 374/16 |
| 0655946 | 4/1979 | U.S.S.R. | 374/16 |
| 0789715 | 12/1980 | U.S.S.R. | 374/16 |
| 0922600 | 4/1982 | U.S.S.R. | 374/16 |

*Primary Examiner*—Daniel M. Yasich
*Attorney, Agent, or Firm*—Griffin, Branigan & Butler

[57] ABSTRACT

In a subject fluid, there is placed an apparatus for measuring a change in state of the fluid, said apparatus having a tubular body which, in turn, contains therein at least one heating sensor employing so-called hot wire method. A quantity of the fluid is introduced into the tubular body and a temperature of the heating sensor is measured by the heating sensor itself as the quantity of the fluid having been introduced into the tubular body is maintained in a state of laminar flow or a static state. The laminar flow is generated by fluid impeller means such as impeller vane, screw-type vane or propeller vane assembly or uniaxial eccentric pump. The static state is maintained y providing gateway means for passage of the fluid into or out from the tubular body and closing such gateway means. A temperature of the fluid having been introduced into the tubular body and maintained in said laminar or static state is measured and discharged out from the tubular body upon completion of said temperature measurements. A change in state of the fluid is determined based on the temperatures of the fluid and the heating sensor.

24 Claims, 16 Drawing Sheets

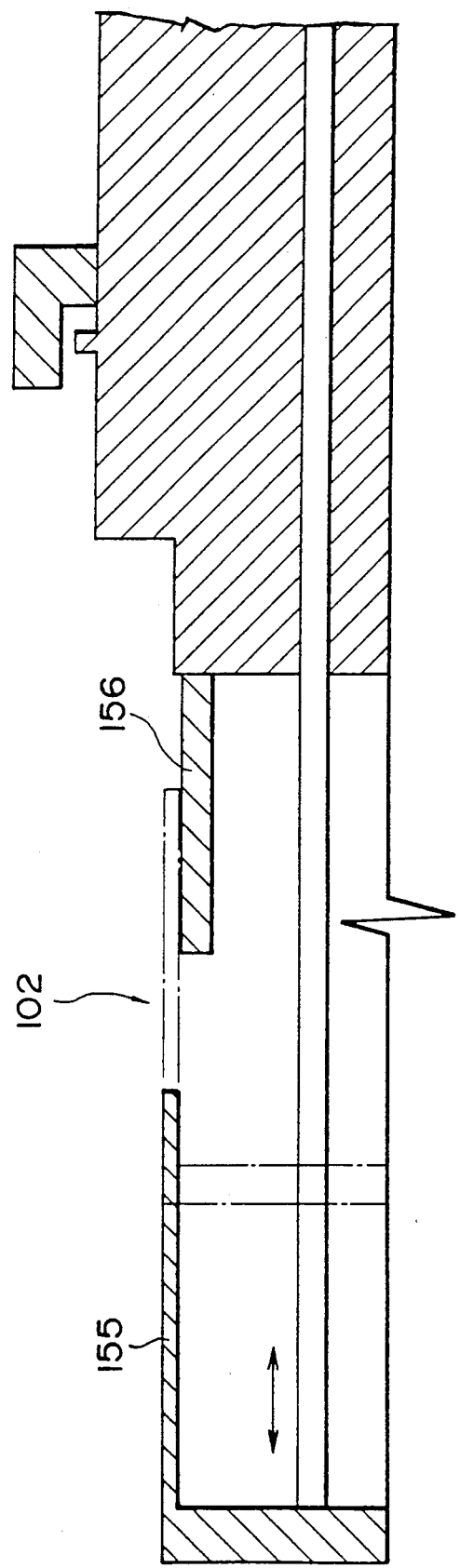

METHOD AND APPARATUS FOR MEASURING A CHANGE IN STATE OF A SUBJECT FLUID

BACKGROUND OF THE INVENTION

The present invention relates to method and apparatus for measuring a change in state, particularly a change in viscosity of a subject fluid utilizing the so-called hot wire method, such method and apparatus being applicable, for example, to determination of a gelation period during a gelation of foodstuff, measurement of a change in viscosity of adhesive, slurry or the like, determination of microorganism density from a change in viscosity due to proliferation of microorganism during a cultivating process, and determination of a microorganism product concentration or the like in relation to a change in viscosity thereof.

Concerning such method and apparatus for measuring a change in state of a subject fluid, various proposals have already been made.

Japanese Utility Model Laid-Open Application No. 1987-126751 discloses a method for measuring a fluid viscosity based on a velocity at which a steel ball falls in a subject fluid.

However, this dynamic method can not be used for a fluid which is susceptible to structural destruction because a steel ball will usually impose a heavy force on the fluid to be measured. In addition, such method requires sampling and therefore makes a continuous measurement impossible. Furthermore, the measurement must be done in an environment free from vibration to insure that the measurement is never affected by a vibration caused by various external factors.

Some of the inventors of the present application have previously disclosed, in Japanese Patent Laid-Open Application No. 1987-185146, a method for measuring a change in state such as viscosity of a subject fluid by measuring a change in heat transfer from a heating element immersed in the subject fluid to the latter.

Such method for measurement is most effectively useful for a static system and further more effectively useful for a state of laminar flow. But in practical use a turbulent flow often must be measured, wherein there is the necessity of providing a stable measurement environment.

To measure a subject fluid in the flowing system, there have already been proposed various methods such as the method adapted to sample a quantity of the flowing subject fluid and then to measure the fluid of the sample in a static system; the method adapted to introduce a quantity of the subject fluid into a bypass within which the actual measurement is made; and the method adapted to make a collective measurement based on outputs from one or more sensors provided within a flowing system. However, the method relying upon sampling is susceptible to generation of microorganism and fluctuations of the measurement depending on the particular location of the system at which said sampling occurs. The method employing the bypass inevitably leads to a complexity of the apparatus and it is often difficult to wash the bypass. And the method employing one or more sensors also requires an apparatus which is correspondingly complicated and sometimes expensive, depending on the number of actually employed sensors, and requires complex analysis of respective output values provided from these sensors.

Some of the inventors of the present application disclosed, in Japanese Patent Laid-Open Application No. 1988-212840, a method for measuring a change in the state of a subject fluid where a quantity of the fluid surrounding a heating sensor is maintained in a state of static flow. Thus, it is possible to measure the state of the fluid, in view of the fact that otherwise there would be generated a turbulent flow around the sensor so that the heat transfer coefficient of fluid would be changed by a change of flow velocity.

With such method of prior art, however, the sensor is susceptible to an unacceptably heavy force imposed by a piston during introduction of the fluid into a tubular body. Additionally, such technique of well known art is unsuitable for fluids of a type such that the quantity of the fluid being present externally of the tubular body tends to exhibit a state continuously changing as the time elapses, because the measurement can be made only within the tubular body.

SUMMARY OF THE INVENTION

Accordingly, it is an object of the invention to achieve an accurate measurement of a change in state of subject fluid, even when a turbulent flow or other conditions of the subject fluid would otherwise make the measurement difficult, by placing a tubular body in the subject fluid and establishing a state of laminar flow or a static state within the tubular body.

The object set forth above is achieved, in accordance with the invention, by a method for measuring a change in state of a subject fluid, comprising steps of:

placing an apparatus for measuring a change in state of the subject fluid, having a tubular body containing there in at least one heating sensor employing so-called hot wire method in the subject fluid, introducing a quantity of the fluid into said tubular body, measuring a temperature of said heating sensor by said heating sensor itself as the quantity of the fluid is maintained in a state of laminar flow or a static state, measuring a temperature of the fluid or the quantity of the fluid within the tubular body, discharging said quantity of the fluid out from the tubular body after said temperature measurements have been completed, and determining a change in state of the subject fluid based on the temperatures of the fluid and the heating sensor.

The object set forth above is realized, according to the invention, by an apparatus for measuring a change in state of a subject fluid, comprising:

a tubular body containing therein at least one heating sensor employing the so-called hot wire method, and fluid impeller means used to generate a laminar flow within said tubular body.

Preferably, an impeller vane assembly, a screw-type vane, a propeller vane assembly or the like is employed as said fluid impeller means.

With the measuring apparatus of such arrangement, a stabilized laminar flow is generated by the fluid impeller means so that said laminar flow can be maintained around the sensors placed within the tubular body during the measurement even if there is a turbulent flow within the fluid tank.

Preferably, the measuring apparatus is incorporated with drive means associated with the fluid impeller means to facilitate movement of the apparatus to any location at which the measurement of a change in state of a subject fluid is to be made.

The fluid impeller means preferably comprises a screw-type vane or a propeller vane assembly adapted to impel the fluid axially of the tubular body so that the fluid can be smoothly introduced into the tubular body in the form of a laminar flow. In this case, there may be provided within the tubular body suitable straightening vanes serving to straighten the fluid axially of the tubular body to make generation of the laminar flow more reliable.

The fluid impeller means may also comprise a flat vane assembly adapted to generate a rotational flow within the tubular body around the axis thereof to insure a stabilized measurement to be performed.

There are provided within the temperature sensor exclusively used to detect a temperature of the fluid and the heating sensor used to detect a temperature of heat generated by itself as this heating sensor is energized for heat generation so that a change in state such as a change in viscosity of the fluid can be determined based on a temperature difference between the fluid and the heating sensor.

In this case, the respective sensors may be oriented to be parallel or perpendicular to a direction in which the fluid flows.

The object set forth above is realized, in accordance with the invention, also by an apparatus for measuring a change in state of a subject fluid, comprising:

a tubular body containing therein at least one heating sensor employing so-called hot wire method, and fluid impeller means used to generate a laminar flow within said tubular body, wherein said tubular body is provided with an inlet and an outlet for the fluid.

With the measuring apparatus of such construction, a change in state of the subject fluid is detected as a quantity of the fluid is impelled by the fluid impeller means into the tubular body so that a flow of a steady velocity is maintained for a reliable measurement even if there is a turbulent flow within the fluid tank.

By providing the fluid temperature sensor exclusively used to detect a temperature of the fluid and the heating sensor used to detect a temperature of heat generated by itself as this heating sensor is energized to generate heat, a change in state such as a change in viscosity of the fluid can be determined from the temperature difference between the fluid and the heating sensor. In this case, the respective sensors preferably extend along a direction in which the fluid flows.

Use of the screw-type vane or the uniaxial eccentric pump allows the subject fluid to be introduced into the tubular body freely from any agitating effect which might impose mechanical shocks upon cells or microorganisms and destroy them.

The object set forth above is realized, in accordance with the invention, also by an apparatus for measuring a change in state of a subject fluid, comprising:

a tubular body containing therein at least one heating sensor employing so-called hot wire method, a gateway for passage of the subject fluid into or out from the tubular body, and means used to open and close said gateway.

With the measuring apparatus of such construction, the gateway is opened, allowing the fluid to pass therethrough into the tubular body and then the gateway is closed to make the fluid static for actual detection of a change in state of the fluid by the sensors. Accordingly, it is assured that the measurement is performed for the quantity of the subject fluid thus static within the tubular body even if there is an instable flow of the fluid within the fluid tank.

When the tubular body consists of an outer tubular element and an inner tubular element and these tubular elements are provided with a plural slits, respectively, so that plural gateways for passage of the fluid into or out from the tubular body are defined by cooperation of said slits, these gateways can be opened or closed in a simple manner. In this case, various arrangements are possible, e.g., an arrangement such that the gateways are opened or closed by axially moving any one of the outer tubular element and the inner tubular element relative to the other or an arrangement such that the gateways are opened or closed by rotating any one of the outer tubular element and the inner tubular element relative to the other. Alternately, the gateways may be provided so as to be opened or closed by partially or entirely moving the wall of the tubular body or pivotally opening or closing the tubular body along a split line extending axially of the tubular body. Further another arrangement is possible in which the tubular body comprises a square tubular body having side walls adapted to be rotated to provide the gateways for the fluid.

Instead of the previously mentioned arrangement in which there are provided within the tubular body the temperature sensor exclusively used to detect a temperature of the fluid and the heating sensor adapted to detect a value of heat generated by itself as this heating sensor is energized to generate heat so that a change in state such as a change in viscosity of the subject fluid can be determined from a temperature difference between the fluid and the heating sensor, an alternate arrangement is also possible in which only the heating sensor is provided within the tubular body so that a fluid temperature is detected by this heating sensor as it is not energized, then the same heating sensor is energized to generate heat and a temperature of this heat is detected by the heating sensor itself. Still another arrangement is also possible in which the heating sensor adapted to detect a temperature of heat generated by itself as it is energized to generate heat is placed within the tubular body while the temperature sensor used only to detect a fluid temperature is placed within or external of the tubular body.

Now a basic principle of the invention will be discussed.

The present invention is based on a method for measuring a change in state of a subject fluid by bringing the subject fluid in thermal contact with a heating element and determining said change from a difference between a temperature of the subject fluid and a temperature of the heating element. As described by some of the inventors of the present application in Japanese Patent Laid-Open Application No. 1987-185146, an apparent viscosity of a fluid changes as a state of this fluid changes. The invention utilizes a method comprising steps of measuring a change in apparent viscosity of a subject fluid and thereby determining a change in state of the fluid, specifically in view of a phenomenon that, during heat transfer from the heating sensor generating a predetermined amount of heat to the fluid, an amount of heat transfer changes and a temperature of the heating sensor correspondingly changes as the apparent viscosity of the fluid changes.

Inversely from the measurement of such changes in temperature, the corresponding change in state of the fluid can be determined. However, the change in temperature is too small for a measurement with a desired accuracy. To magnify such value of changes, it is preferred to employ a heat transfer coefficient α indicating an actual progress of heat transfer.

The heat transfer coefficient α is expressed by a following equation:

$$\alpha = Q/S \, (\theta_s - \theta_\infty)$$

where
Q: heat value generated in the heating element,
S: surface area of the heating element,
$\theta_s$: surface temperature of the heating element,
$\theta_\infty$: temperature of surrounding fluid.

When a change in the fluid temperature is enough small to consider the heat value generated in the heating element as being constant, a temperature difference between the heating element and the fluid is measured as the time elapses and a change in such temperature difference may be measured to determine a change in state of the fluid.

When a change in the fluid temperature is relatively large, and a electrical resistance value R changes as the fluid temperature changes according to an equation $$Q = R_i^2$$

where
R: electrical resistance value of the sensor,
i: electrical current density applied to the sensor,
the heat value which would otherwise change due to said change in the electrical resistance value may be maintained constant by controlling the electrical current density value i.

It should be understood that the surface temperature ($\theta_s$) of the sensor can be easily calculated from the temperature ($\theta_w$) of the heating sensor utilizing the invention disclosed by members forming a part of the inventors of the present application in U.S. Pat. No. 4,832,504.

It is also possible to determine a concentration of the fluid in correlation with various factors such as said temperature of the heating sensor, and changes in heat transfer coefficient as well as viscosity of the fluid.

State of fluid depends also on, in addition to the change in viscosity, changes in composition, physical property or the other factors of the fluid. Accordingly, it is also possible to determine a change in state of various subject fluids by relating index values obtained from, in addition to the heat transfer coefficient, thermal diffusivity, thermal conductivity, volumatic expansion or the like.

BRIEF DESCRIPTION OF THE DRAWINGS

The above and other objects of the invention will be seen by reference to the description taken in connection with the accompanying drawings, in which:

FIG. 18 is a sectional view, partially broken away, illustrating an embodiment of the measuring apparatus constructed in accordance with the invention, in which a front half section of the tubular body is axially slidable.

DETAILED DESCRIPTION OF THE INVENTION

Figure 1:
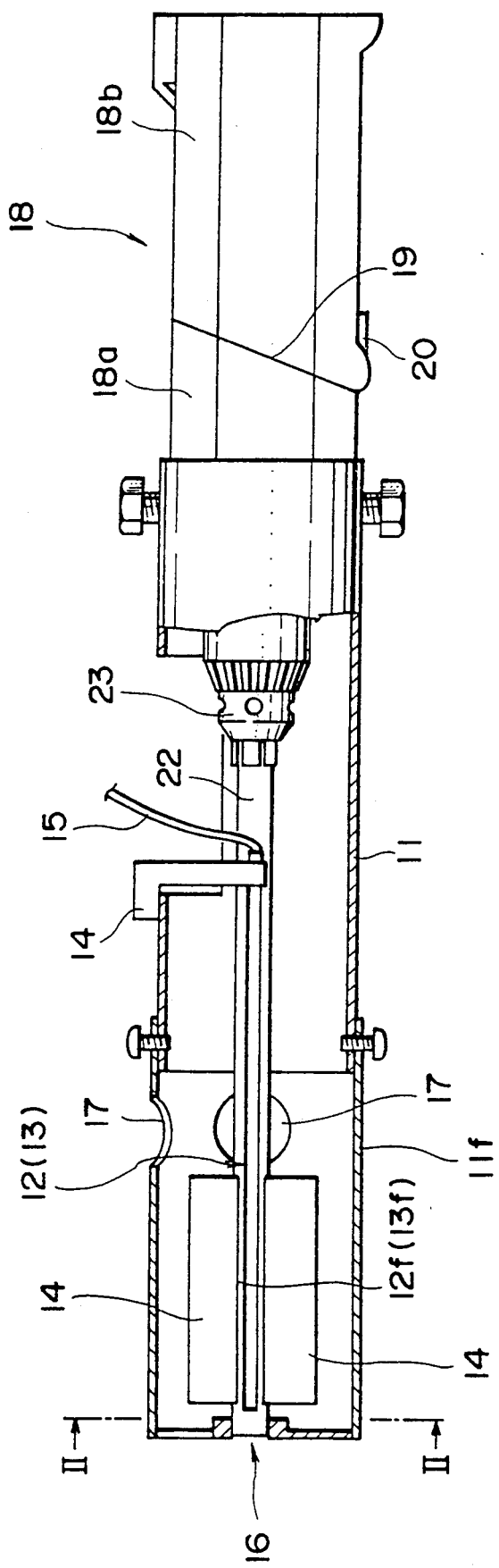
FIG. 1 is a side view illustrating, partially in section, an embodiment of the apparatus constructed in accordance with the invention, employing an impeller vane assembly as fluid impeller means.

The invention utilizes a method for measuring a change in state of a subject fluid on the basis of a temperature difference between the heating element and the fluid. Initially, an embodiment of the invention will be described, which comprises a tubular body provided therein with an impeller vane assembly adapted to generate a laminar flow in the fluid and with a sensor serving to determine an actual state of the fluid.

Referring to FIGS. 1 through 5 illustrating a first embodiment of the invention employing the fluid impeller means of a specific type. A sensor 12 serving as a heating element and a sensor 13 serving to detect a temperature of the fluid are placed within a tubular body 11 and fixed by a bracket 14 with respect to said tubular body 11. A lead wire 15 is electrically connected to a controller (not shown).

The sensors 12, 13 have respective front sections serving as detectors 12f, 13f located within a leading section 11f of the tubular body 11.

The leading section 11f of the tubular body 11 has an opening 16 in a front end surface thereof, through which a subject fluid is introduced into the tubular body 11 so as to be measured by the sensors 12, 13 therein. The subject fluid thus introduced into the tubular body 11 will be discharged through an outlet port 17.

A gripper 18 is mounted on a base end of the tubular body 11. In this embodiment, the gripper 18 comprising a gripper proper 18a and a grip 18b is so arranged that said grip 18b may be pivotally rotated relative to the gripper proper 18a at a diagonal joint 19 to provide an angular configuration. The gripper 18 is held by a stopper 20 in this angular configuration.

The gripper proper 18a contains an electromotor (not shown) while the grip 18b contains a battery (not shown) so that, upon actuation of a switch 21, the electromotor is actuated to drive a rotational shaft 22 within the tubular body 11. The rotational shaft 22 is coupled by a chuck 23 to a drive shaft of the electromotor.

Figure 2:
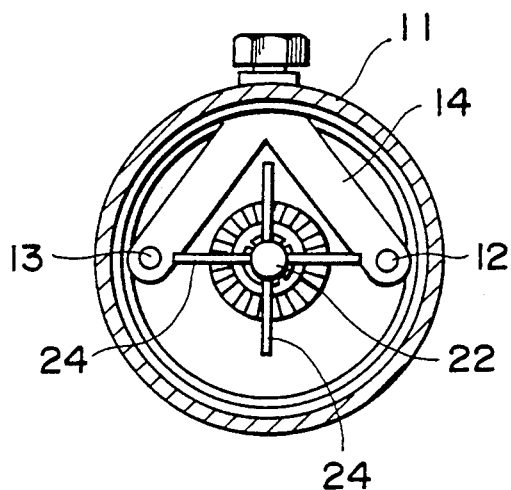
FIG. 2 is a sectional view taken along a line II—II in FIG. 1.
Figure 3:
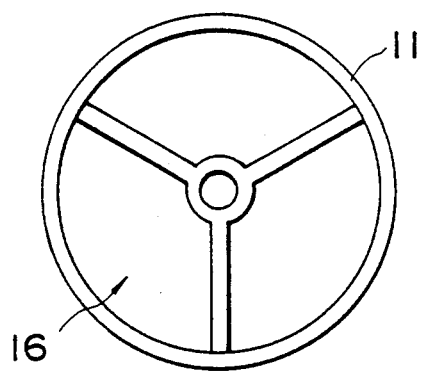
FIG. 3 is a front view of the embodiment illustrated by FIG. 1 with the internal details being omitted.
Figure 4:
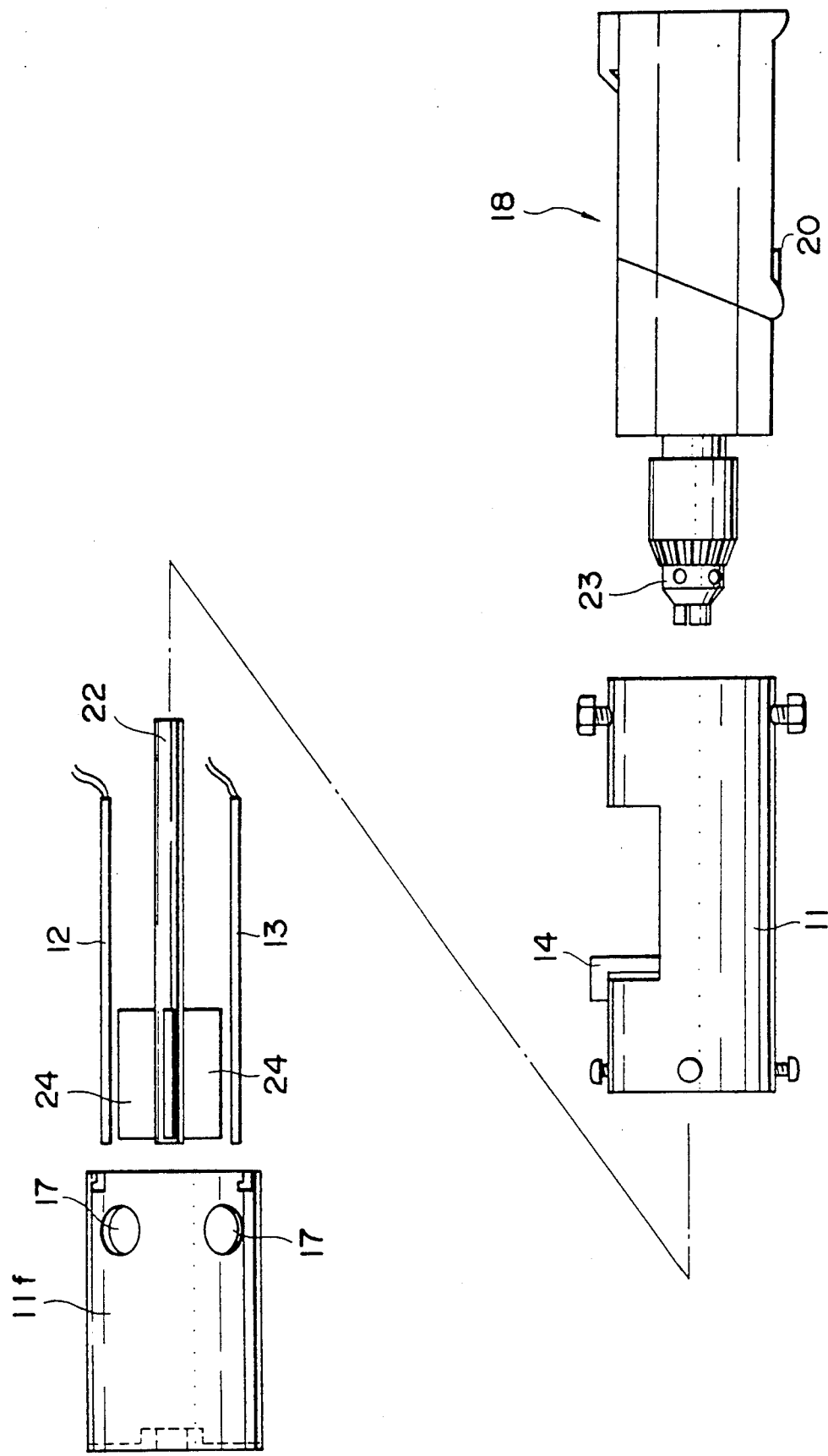
FIG. 4 is an exploded side view of the embodiment illustrated by FIG. 1.
Figure 5:
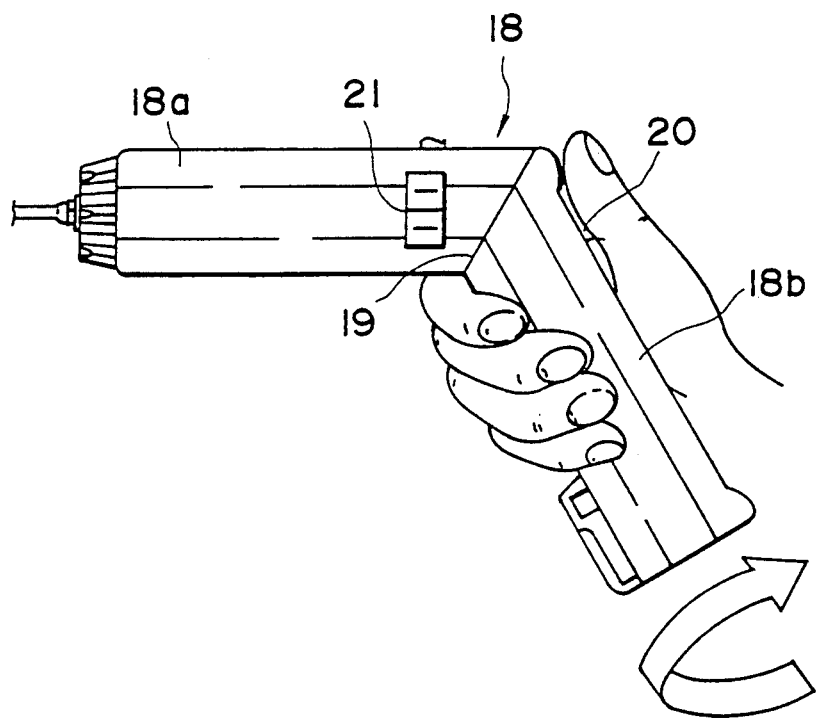
FIG. 5 is a side view illustrating a grip in the embodiment illustrated by FIG. 1.

The rotational shaft 22 is provided on its leading section with four individual flat vanes 24 so as to be surrounded by the leading section 11f of the tubular body 11. It should be noted that these individual vanes 24 are, as seen in FIG. 2, located radially inside of the sensors 12, 13 and therefore free from contact therewith.

In this manner, actuation of the switch 21 causes the impeller vane assembly 24 to be rotated, generating a rotational flow within the tubular body 11 and driving the fluid perpendicularly against the respective sensors 12, 13. The impeller vane assembly 24 may be of various configurations and the direction of a flow generated within the tubular body 11 depends on the particular configuration of this impeller vane assembly.

Figure 6:
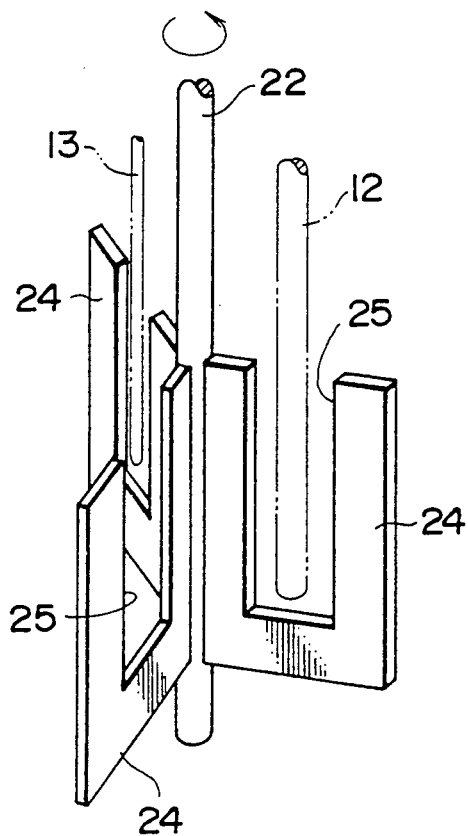
FIG. 6 is a perspective view illustrating another embodiment of the fluid impeller means.

FIG. 6 illustrates a second embodiment of the fluid impeller means according to the invention, comprising three individual flat vanes each having a radial length slightly smaller than the inner diameter of the tubular body 11 and formed with a slit 25 to prevent the vane from being contacted by the sensors 12, 13.

Figure 7:
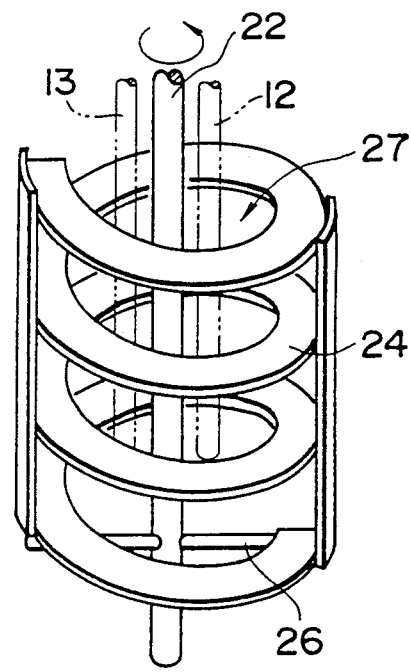
FIG. 7 is a perspective view of a helical vane assembly as still another embodiment of the fluid impeller means.
Figure 10:
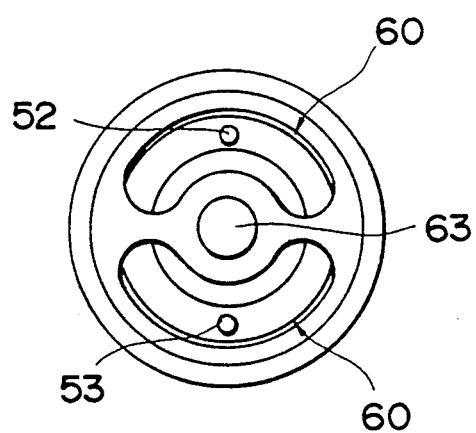
FIGS. 9 and 10 are a partial sectional side view and a front view, respectively, illustrating an embodiment of the measuring apparatus constructed according to the invention, employing a screw-type vane as the fluid impeller means.

FIG. 7 illustrates a third embodiment of the fluid impeller means according to the invention, comprising a single helical impeller vane 24 fixed by a supporting lever 26 to the rotational shaft 22. This helical vane 24 defines a central free space 27 in which there are provided the sensors 12, 13 so that the helical vane 24 can be rotated without being contacted by these sensors 12, 13. Alternately, the sensors 12, 13 may be located outside of the helical vane 24.

Rotation of this helical vane 24 generates a flow of the fluid passing through the opening 16 (see FIG. 1) formed in the front end surface of the tubular body 11 thereinto and then axially within said tubular body 11 along the sensors 12, 13.

Figure 8:
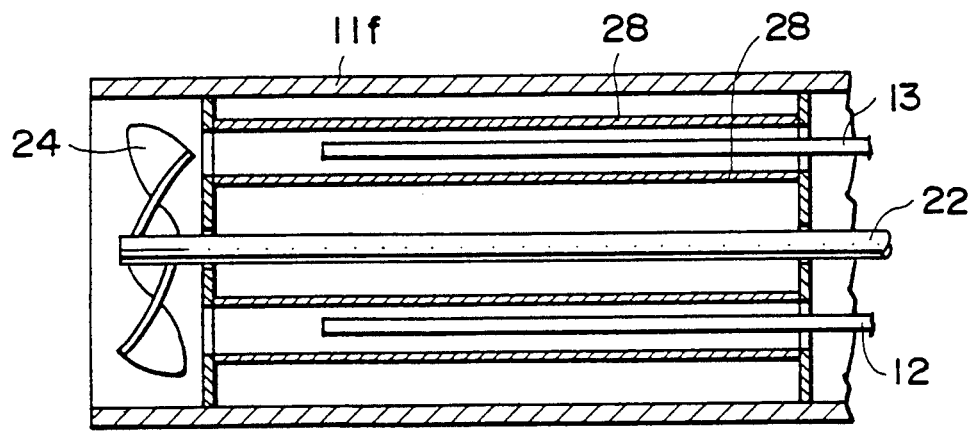
FIG. 8 is a sectional view illustrating a propeller vane assembly as further another embodiment of the fluid impeller means.

FIG. 8 illustrates a fourth embodiment of the fluid impeller means according to the invention comprising so-called propeller vane assembly mounted on the front end of the rotational shaft 22 to introduce the fluid into the tubular body 11. Furthermore, the leading section 11f of the tubular body 11 contains straightening vanes 28 used to straighten a flow of the fluid introduced by the propeller vane assembly 24 into the tubular body 11 and thereby to assure that the fluid axially flows within the tubular body 11. Rotation of this propeller vane assembly 24 causes the fluid to be introduced into the tubular body 11 and then to flow axially within the tubular body 11 along the sensors 12, 13.

The measuring apparatus including any one of the above-mentioned first through fourth embodiments of the fluid impeller means constructed according to the invention may be operated in a manner as will be described below.

With the grip 18b of the gripper 18 in a hand, the leading section 11f of the tubular body 11 is immersed into a subject fluid allowing the latter to be introduced into the tubular body 11 through the opening 16 and then the switch 21 is turned ON to rotate the fluid impeller means 24 so that a rotational flow or an axial flow is generated and there by the fluid is moved in perpendicularity to or in parallel with the sensors 12, 13.

Then, a temperature of the fluid is measured by the fluid temperature sensor 13 while the fluid is supplied with heat from the heating sensor 12 and a change in state of the fluid such as a viscosity is determined from a temperature difference between the heating sensor and the fluid surrounding said fluid temperature sensor.

The respective sensors are preferably arranged so as to extend along or perpendicularly to a direction in which the fluid flows.

This handy apparatus equipped with drive means for the impeller vane assembly can be easily moved to any desired location at which a state of the fluid is to be determined and allows a stabilized measurement to be achieved by generating a stabilized rotational flow or axial flow within the tubular body 11 under action of the fluid impeller means 24.

Accordingly, it is possible to perform the desired measurement with the fluid surrounding the sensors being maintained in a state of laminar flow, even when there is a turbulent flow within a fluid tank.

In the particular embodiment comprising the single helical impeller vane or the propeller vane assembly as the fluid impeller means, the tubular body 11 preferably contains therein the straightening vanes adapted to straighten a flow of the fluid axially of the tubular body 11 so that the laminar flow is further reliably generated.

Use of the impeller vane assembly comprising individual flat vanes allows a stabilized rotational flow to be generated within the tubular body 11 and thereby allows a reliable measurement to be achieved.

The fluid impeller means may be implemented also in an arrangement different from those as illustrated and described herein.

Figure 9:
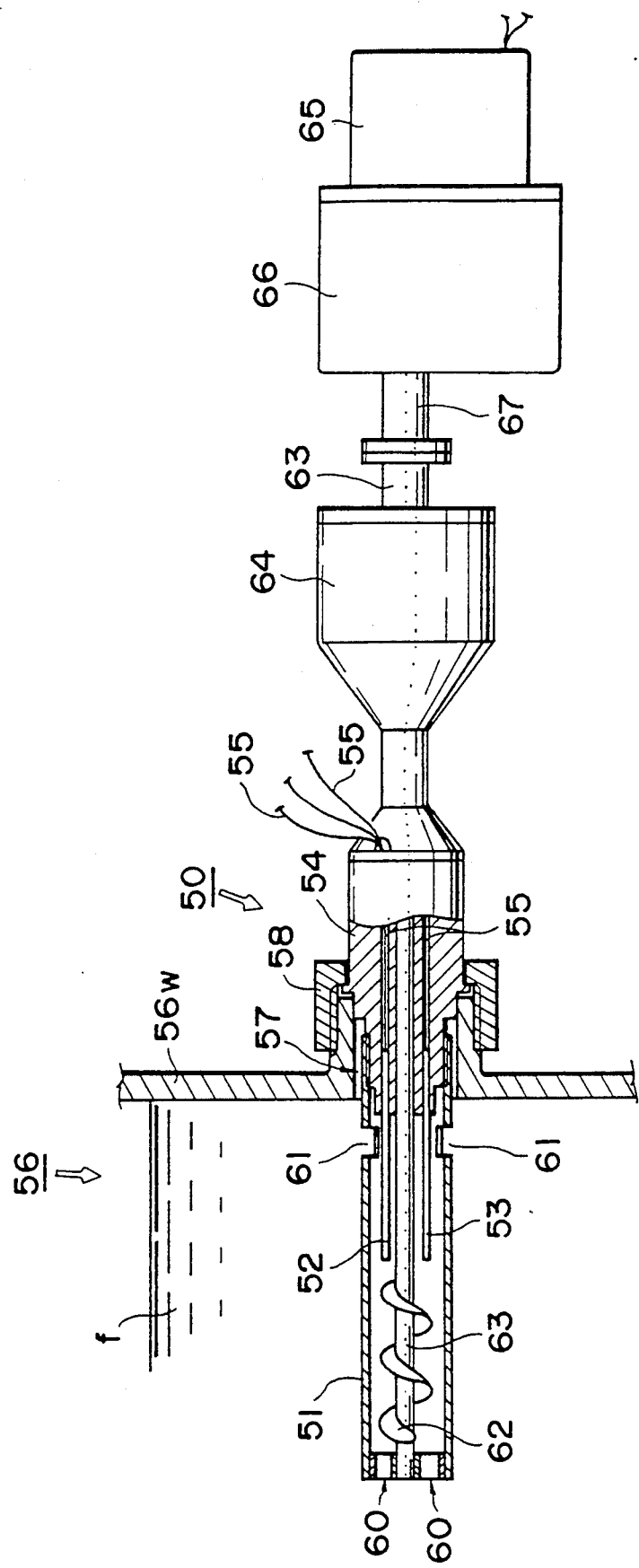

FIG. 9 illustrates, in a section, a fifth embodiment of the measuring apparatus constructed according to the invention, which adopts a screw-type vane as the fluid impeller means to generate a laminar flow of the subject fluid within the tubular body.

Referring to FIG. 9, a measuring apparatus 50 includes a tubular body 51 and is connected to a fluid tank 56. A heating sensor 52 and a fluid temperature sensor 53 are held by a common sensor support 54 within the tubular body 51 in parallel to the axis of the tubular body 51. A lead wire 55 is drawn out through a rear end of the sensor support 54 and electrically connected to a controller (not shown).

The sensor support 54 is inserted into a connecting port 57 formed through a wall 56w of the fluid tank 56 and held in position by a clamp ring 58 so that the tubular body 51 is immersed in a subject fluid f with which the tank 56 has been filled.

The tubular body 51 is provided in its front end surface with an inlet 60 and adjacent its rear end with an outlet 61. The tubular body 51 contains therein a screw-type vane 62 extending axially of the tubular body 51 and rotation thereof causes the subject fluid f to be introduced into the tubular body 51 through the inlet 60, then to flow along the sensors 52, 53 and to be discharged through the outlet 61.

A rotational shaft 63 of the screw-type vane 62 projects from a rear end of mechanical seal means 64 provided behind the sensor support 54 and is connected to an output shaft 67 of a gear box 66 that is driven by an electromotor 65.

The instant embodiment allows the sensors 52, 53 to detect any change in a state of the subject fluid f as the screw-type vane 62 impels the fluid f within the tubular body 51 in parallel to the sensors 52, 53. Even when a turbulent flow is being generated in the fluid f within the fluid tank 56, the flow of a constant velocity is maintained within the tubular body 51 and therefore changes in concentration, viscosity and the like of the fluid f can be determined through a stabilized process of measurement.

Figure 11:
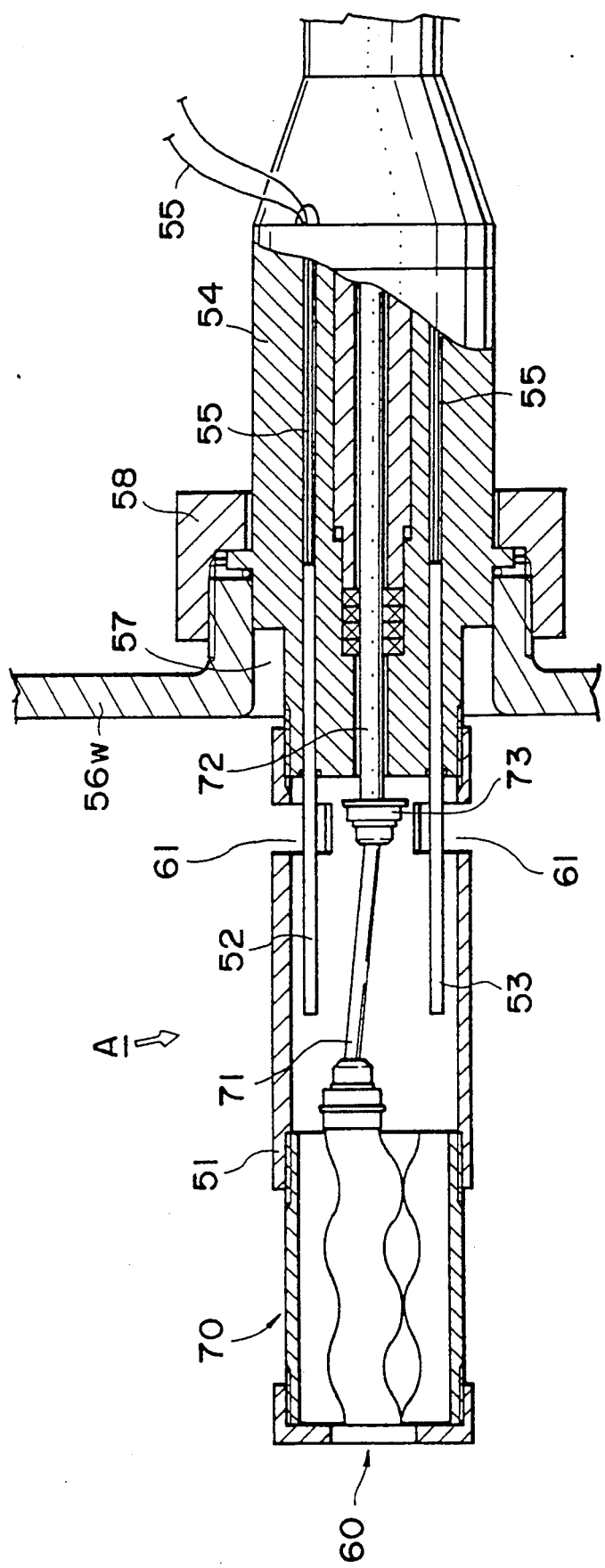
FIG. 11 is a side view illustrating, partially in section, an embodiment of the measuring apparatus constructed in accordance with the invention, employing a uniaxial eccentric pump as the fluid impeller means.

FIG. 11 illustrates a sixth embodiment closely related to the fifth embodiment, in which the tubular body 51 is provided at its front end with a uniaxial eccentric pump 70. An eccentric shaft 71 used to actuate the uniaxial eccentric pump 70 is coupled by a coupling 73 to a rotational shaft 72. The rotational shaft 72 projects, just as in the case of FIG. 9, from the rear end of the mechanical seal means (not shown in FIG. 11) provided behind the sensor support 54 and is connected to the output shaft of the gear box driven by the electromotor.

The remainder of the structure is identical to that as shown by FIG. 9.

Also the embodiment illustrated by FIG. 11 allows the sensors 52, 53 to detect any change occurring in a state of the subject fluid f as the uniaxial eccentric pump 70 impels the fluid f to flow within the tubular body 51 at a constant flow velocity for the stabilized process of measurement.

Figure 12A:
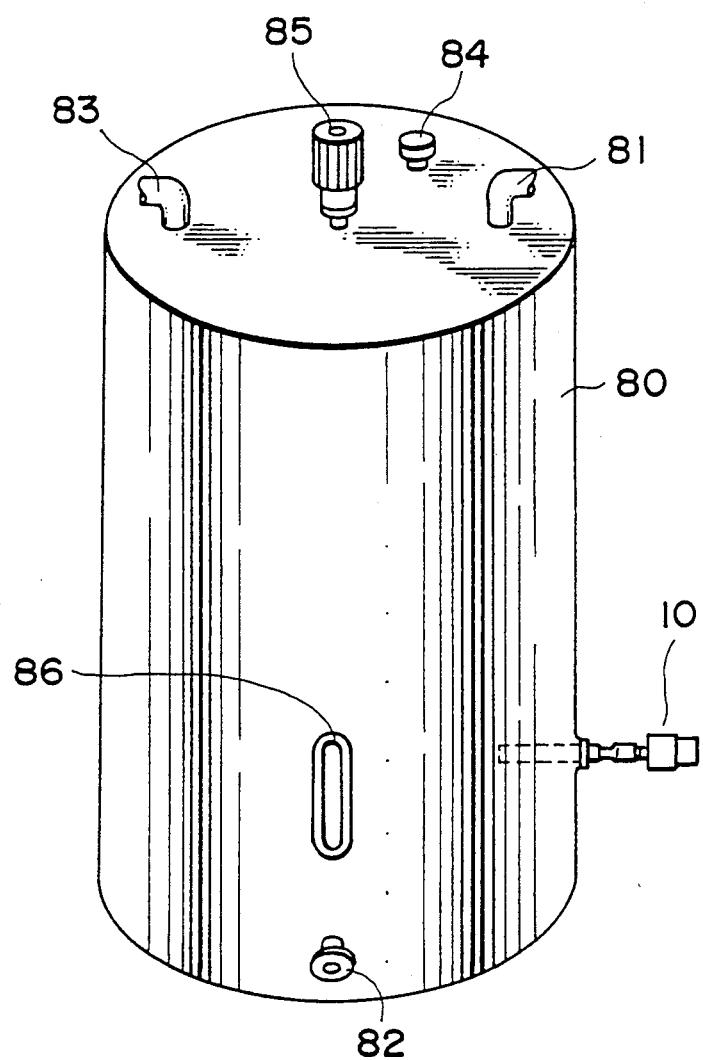
FIGS. 12A through 12C are perspective views illustrating manners in which the measuring apparatus of the invention employing the screw-type vane or the uniaxial eccentric pump as the fluid impeller means may be mounted on an associated fluid tank, respectively.
Figure 12B:
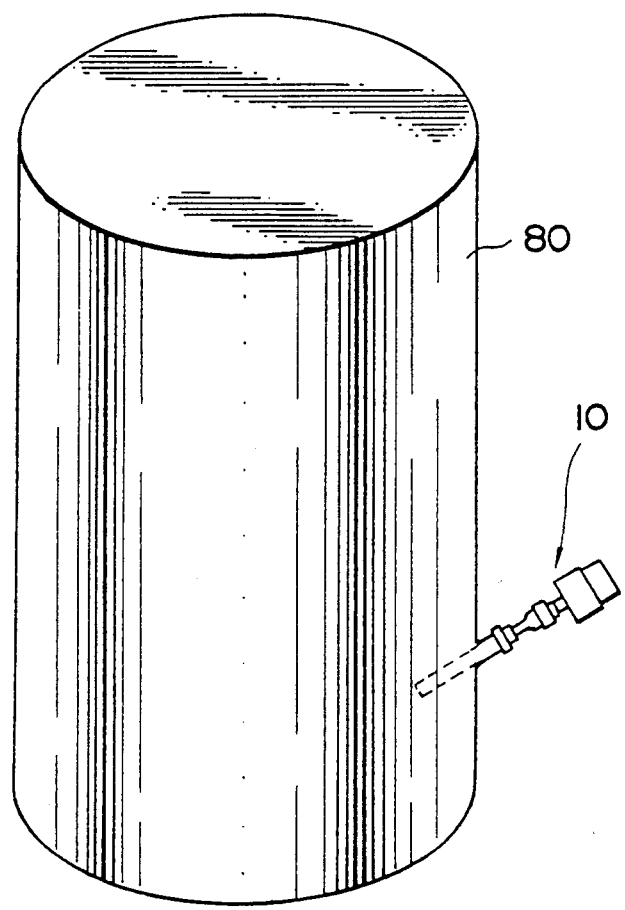
Figure 12C:
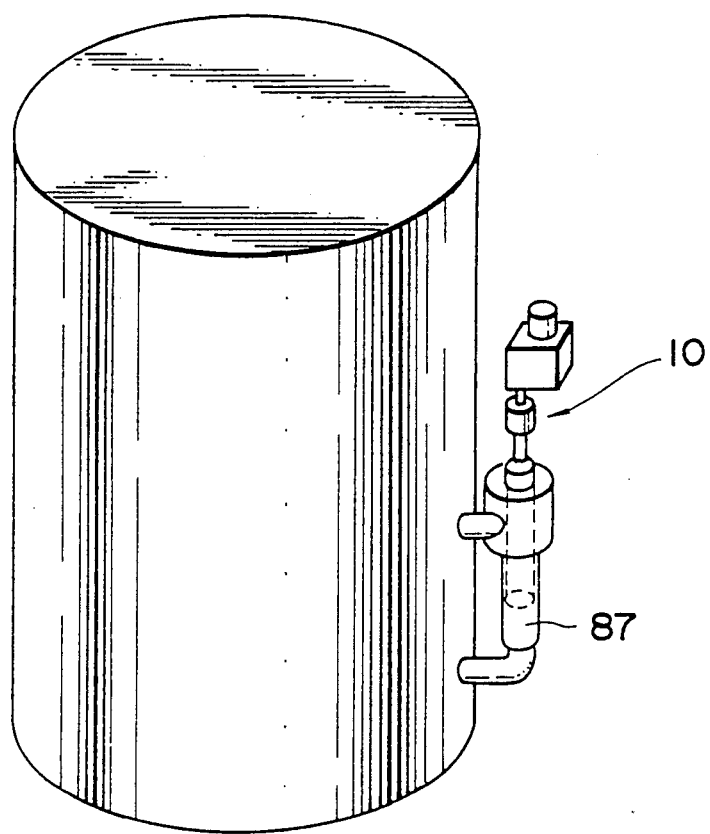

FIGS. 12A through 12C are perspective views illustrating possible manners in which the measuring apparatus 10 of the invention may be mounted on a system filled with a subject fluid, taking a cell cultivator tank 80 as a specific example. As seen in FIG. 12A, the cell cultivator tank 80 is provided with an inlet 81 and a drain 82 for a subject fluid f, a gas inlet 83, a gas outlet 84, an agitator 85, a viewing window 86, etc. (These components are not shown in FIGS. 12B and 12C.)

FIG. 12A shows the measuring apparatus 10 mounted on the cell cultivator tank 80 in a horizontal orientation with respect to the tank 80, FIG. 12B shows the measuring apparatus 10 mounted on the cell cultivator tank 80 with the inlet 60 opening at the leading end of the measuring apparatus 10 slightly inclined downward, and FIG. 12C shows the measuring apparatus 10 mounted in a bypass 87 provided laterally of the cell cultivator tank 80 for circulation of the fluid.

The measuring apparatus 10 of the invention may be mounted on the associated system selectively in any one of the manners as illustrated by FIGS. 12A through 12C. Additionally, even when there is a turbulent flow of the fluid within the tank such as the cell cultivator tank 80 due to agitation of the fluid by the agitator 85, the sensors 52, 53 reliably detect change in a state of the fluid f such as a change in the concentration, since the screw-type vane 62 or the uniaxial eccentric pump 70 generates a stabilized laminar flow of a constant velocity within the tubular body 51.

Still another embodiment of the invention will be discussed, in which the tubular body is provided with gateways for a subject fluid and these gateways are arranged to be selectively opened or closed.

Figure 13:
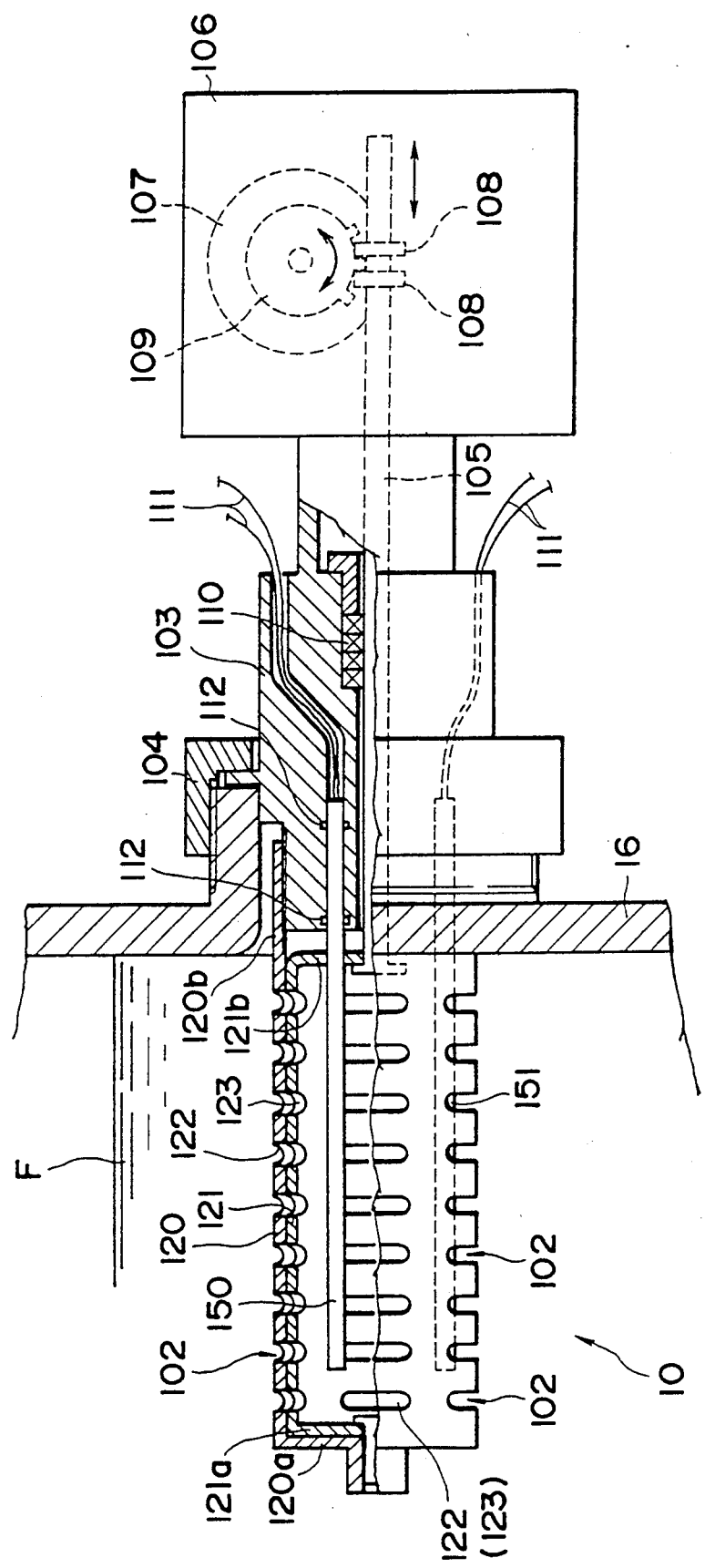
FIGS. 13 and 14 are side views illustrating, partially in section, an embodiment of the measuring apparatus constructed according to the invention comprising an outer tubular element and an inner tubular element both provided with slits, in opened and closed positions, respectively.
Figure 14:
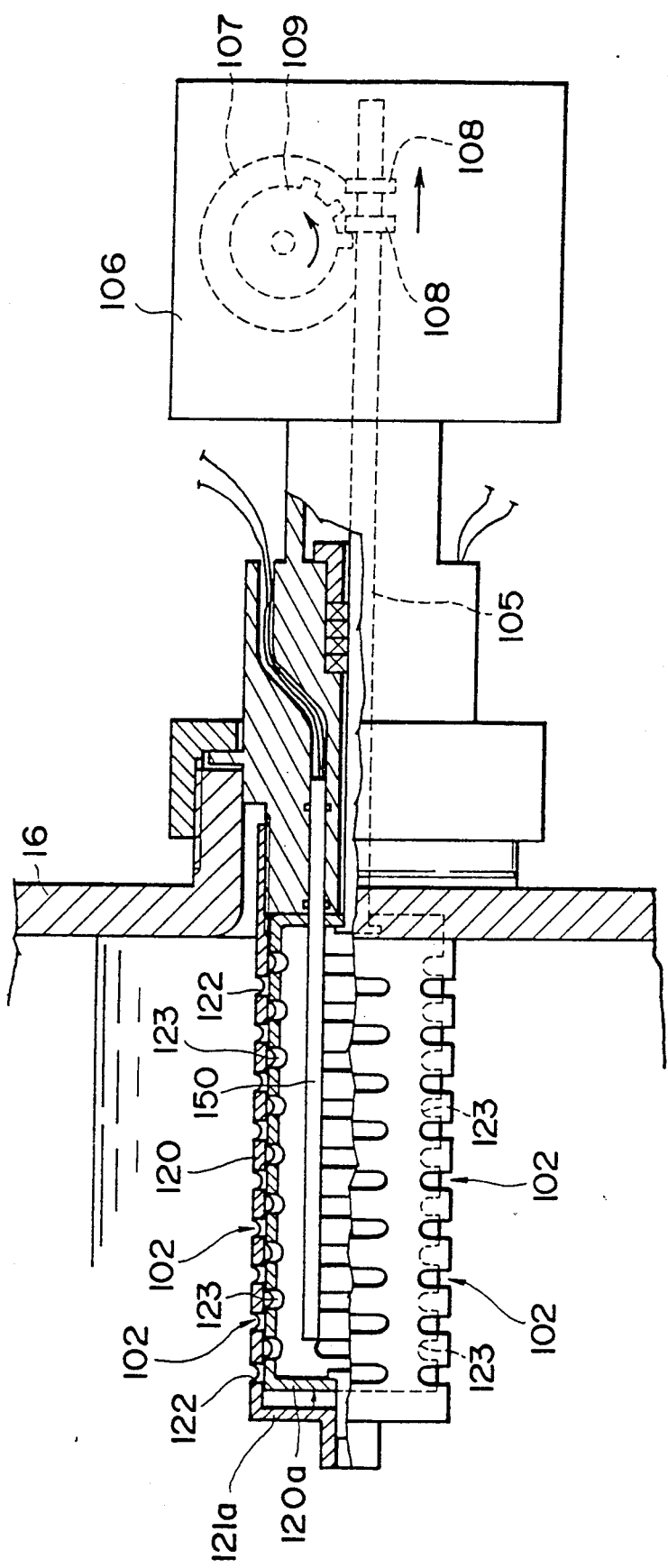

FIGS. 13 and 14 illustrate such embodiment as a seventh embodiment of the invention. The measuring apparatus 10 is shown as being mounted on the wall of the fluid tank 16 filled with the subject fluid F. A tubular body 101 defines therein a space within which the fluid F stays. The tubular body 101 consists of an outer tubular element 120 and an inner tubular element 121 with said inner tubular element 121 being axially movable within the outer tubular element 120. These outer tubular element 120 and inner tubular element 121 are formed therearound with a plurality of circumferential slits 122, 123, respectively, both serving to define the gateways for the fluid F.

As will be apparent from FIG. 13, so long as a front end wall 121a of the inner tubular element 121 is in contact with a front end wall 120a of the outer tubular element 120, said slits 122 are aligned with said slits 123 and the gateways are opened to the maximum area for passage of the fluid F into or out from the tubular body. A base end 120b of the outer tubular element 120 is secured around a sensor support 103 which is, in turn, secured by bolts 104 to the wall of the fluid tank 16. A shaft 105 extends through the sensor support 103 and has its front end secured to a base end 121b of the inner tubular element 121. There is provided behind the measuring apparatus 10 a drive mechanism 106 containing therein an electromotor 107 adapted to rotate a ratchet wheel 109 in engagement with protrusions 108 formed around the shaft 105. Said slits 122, 123 are progressively displaced out of the mutual alignment as the shaft 105 is moved rearward in operative association with rotation of the ratchet wheel 109, until the gateways 102 are fully closed, as shown in FIG. 14. Reference numeral 110 designates a packing. A pair of sensors 150, 151 axially extend within the inner space of the tubular body 101. The sensor 150 is the heating sensor adapted to generate heat and to detect a change in temperature of this sensor itself and the sensor 151 is the fluid temperature sensor adapted to detect a temperature of the fluid surrounding this sensor. Reference numeral 111 designates lead wire serving to energize the sensors 150, 151 and also to measure a value of voltage applied to these sensors. The lead wire 111 is electrically connected to the controller or the like (not shown). Reference numeral 112 designates packings.

Figure 15:
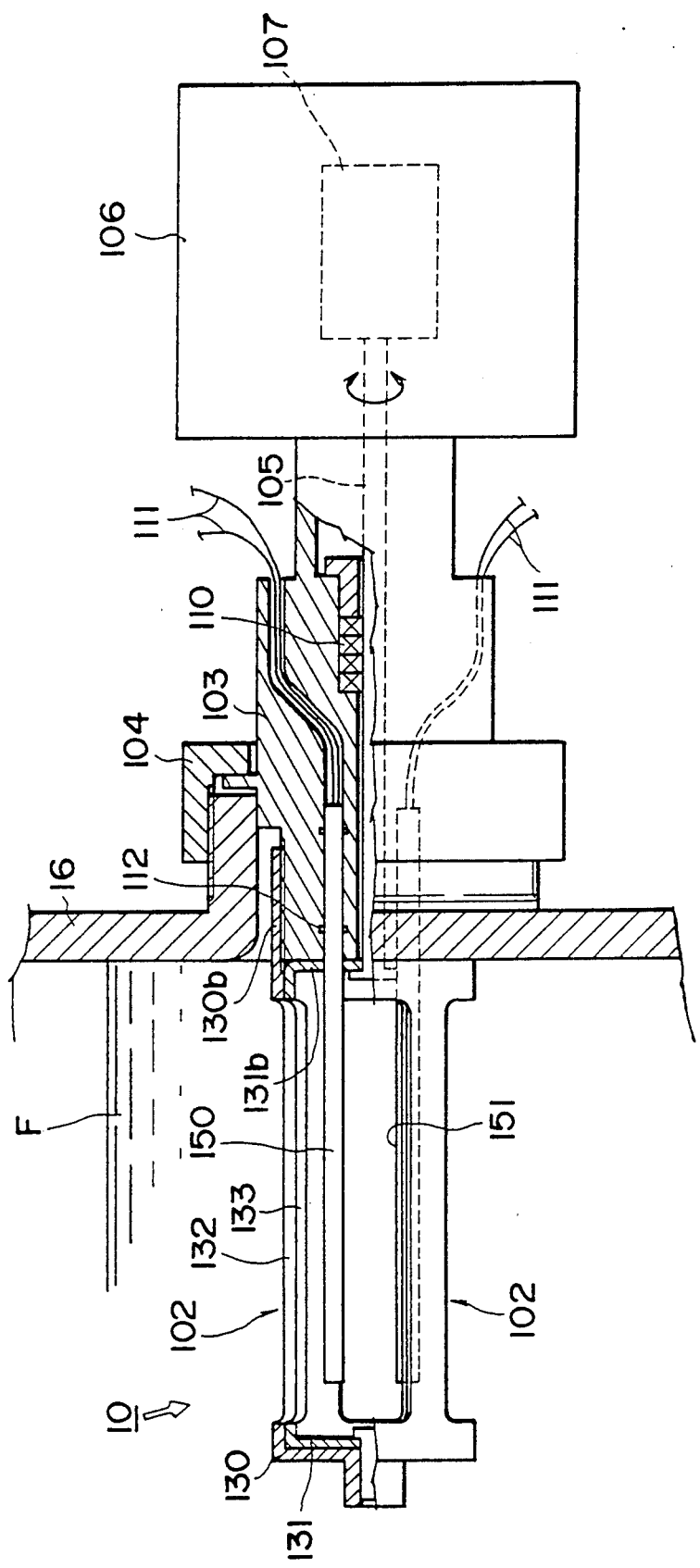
FIG. 15 is a side view illustrating, partially in section, an embodiment of the measuring apparatus constructed according to the invention comprising outer and inner tubular elements both provided with axial slits.

FIG. 15 shows a eighth embodiment closely related to the seventh embodiment of the measuring apparatus constructed in accordance with the invention, in which the tubular body 101 consists of an outer cylindrical element 130 and an inner cylindrical element 131 with the inner cylindrical element 131 being rotatable within the outer cylindrical element 130 to open or close the gateways for the fluid F.

Specifically, the outer cylindrical element 130 and the inner cylindrical element 131 are provided therearound with a plurality of axial slits 132, 133 respectively, thereby defining the gateways 102 for the fluid F. When these slits 132, 133 are completely aligned, as seen in FIG. 15, the gateways 102 are opened to the maximum degree for passage of the fluid F into or out from the tubular body. The outer cylindrical element 130 has its base end 120b secured around the sensor support 103 which is, in turn, secured by the bolts to the wall of the fluid tank 16. The front end of the shaft 105 extending through the sensor support 103 is mounted on a base end 131b of the inner cylindrical element 131 and rotatably driven by the electromotor 107 contained within the drive mechanism 106 for the apparatus. Thereby the inner cylindrical element 131 is rotated within the outer cylindrical element 130. Said slits 132, 133 are displaced out of said mutually aligned relationship as the inner cylindrical element 131 is rotated relative to the outer cylindrical element 130, until the gateways 102 are fully closed. The other components are similar to those as have been mentioned in reference with FIG. 13, i.e., this embodiment also includes the heating sensor 150, the fluid temperature sensor 151, the lead wire 111 electrically connected to the controller or the like (not shown), and the packings 110, 112.

Figure 16:
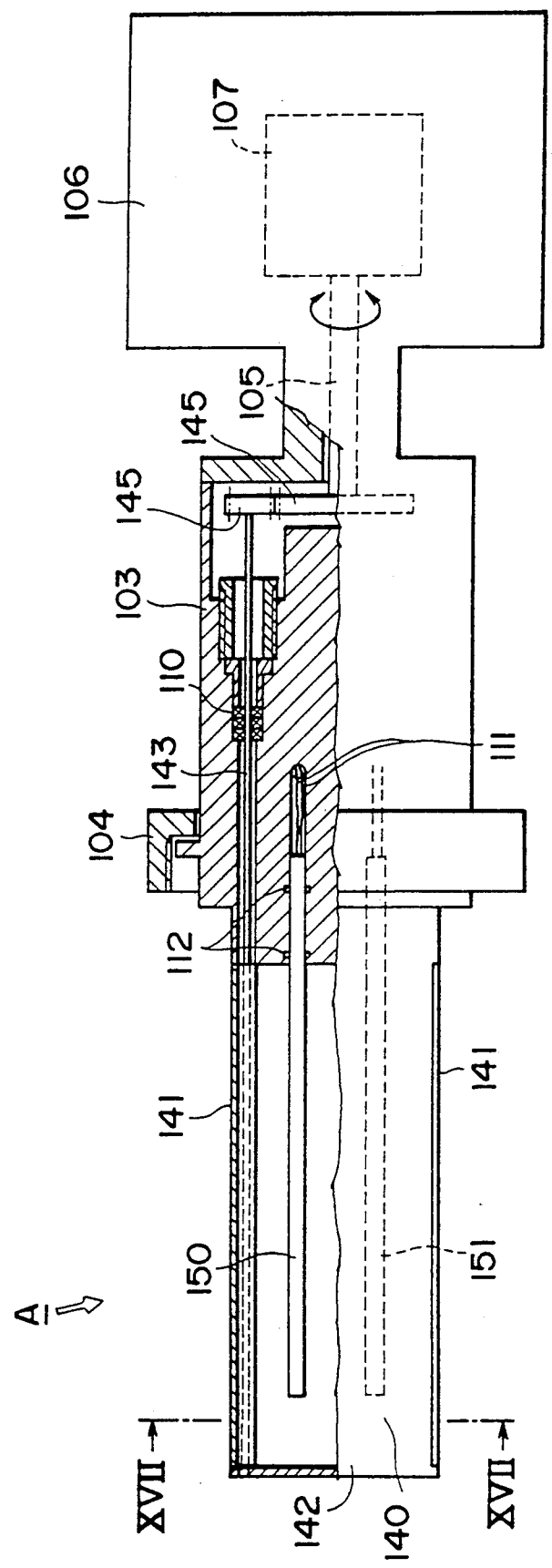
FIG. 16 is a side view illustrating, partially in section, an embodiment of the measuring apparatus constructed according to the invention, in which the tubular body comprises a square tubular body having its vertically opposite side walls adapted to be rotated so as to open or close gateways for the fluid.
Figure 17:
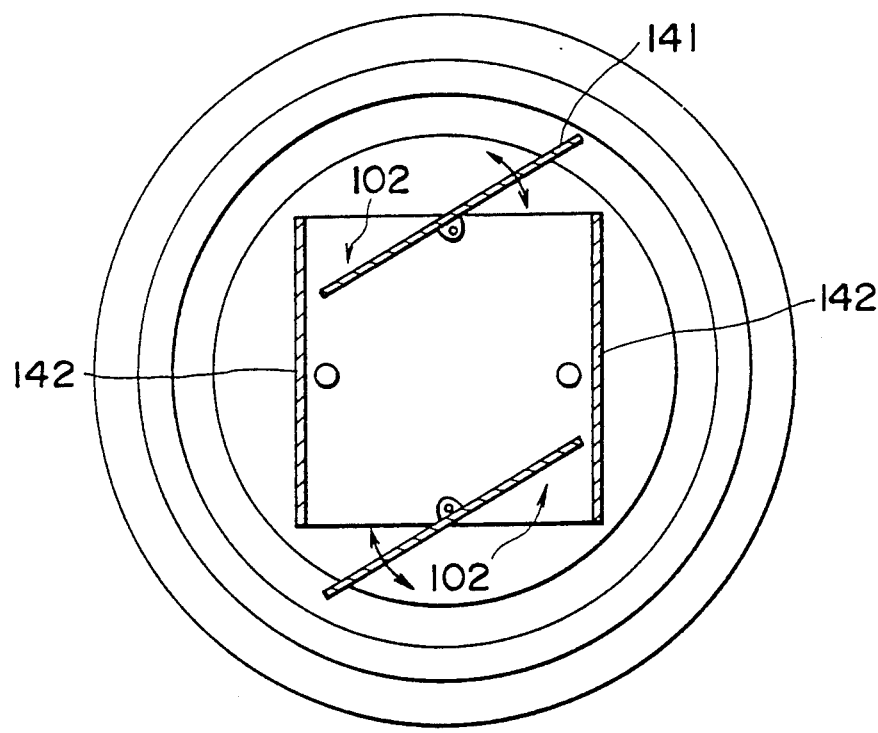
FIG. 17 is a sectional view taken along a line XVII—XVII in FIG. 16.

FIGS. 16 and 17 illustrate a ninth embodiment closely related to the seventh embodiment of the invention, in which a tubular body 140 comprises a square tubular body having vertically opposite sides 141, 141 and laterally opposite sides 142, 142. Gateways for the fluid F are opened or closed by rotating the vertically opposite sides 141, 141.

More specifically, the tubular body 140 is secured at the laterally opposite sides 142, 142 to the sensor support 103 which is, in turn, secured by the bolts 104 to the wall of the fluid tank 16. The vertically opposed sides 141, 141 are rotatably mounted on respective rotational shafts 143 which are operatively associated by gears 144, 145 with the rotational shaft 105 driven by the electromotor 107. The gateways 102 are held closed so long as the vertically opposed sides 141, 141 are in their horizontal positions and the fluid F can not flow into or out from the tubular body 140. The gateways 102 are opened as the electromotor 107 is actuated to rotate the vertically opposed sides 141, 141 from said respective horizontal positions to their inclined or vertical positions, allowing the fluid F to flow into or out from the tubular body 140 (See FIG. 17). The other components are similar to those as have been mentioned with reference to FIG. 13, i.e., this embodiment also includes the heating sensor 150, the fluid temperature sensor 151, the lead wire 111 electrically connected to the controller or the like (not shown), and the packings 110, 112.

FIG. 18 illustrates a tenth embodiment closely related to the seventh embodiment of the measuring apparatus 10 constructed in accordance with the invention, in which the tubular body consists of a front half section 155 and a rear half section 156 with said front half section 155 being slidably movable forward relative to the rear half section 156 to open the gateways 102 and rearward relative to the rear half section 156 to close the gateways 102.

Figure 19:
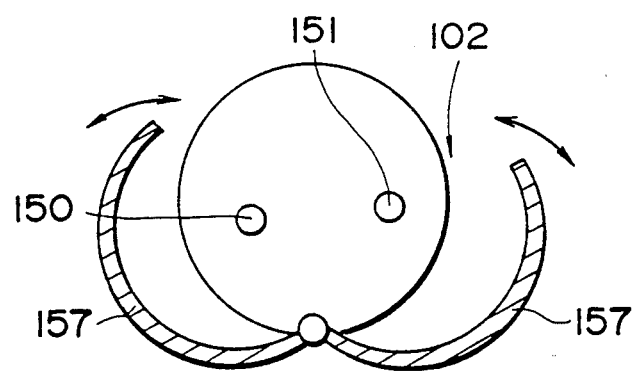
FIG. 19 is a front view illustrating, partially in section, an embodiment of the measuring apparatus constructed in accordance with the invention, in which the cylindrical wall of the tubular body is split along a split line extending axially of the tubular body and can be laterally opened pivotally around a line extending diametrically opposed to said split line.

Finally, FIG. 19 shows an eleventh embodiment being also closely related to the seventh embodiment of the invention, in which the gateway 102 for the fluid F is defined by a split line axially extending through a cylindrical wall 157 of the tubular body along which the tubular body can be pivotally opened or closed around a pivot line axially extending through the wall diametrically opposed to said split line.

With the seventh through eleventh embodiments of the invention as have been discussed above, the gateways 102 are opened to introduce the subject fluid F into the tubular body and then the gateways 102 are closed to immobilize the fluid F before the measurement is initiated. Thereafter the heating sensor 150 is energized to generate heat and the heat thus generated is measured while a temperature of the fluid F is measured by the fluid temperature sensor 151. Then a state of the fluid is determined from a temperature difference obtained from these sensors.

In this manner, a stabilized process of measurement is assured by maintaining the fluid F immobilized within the tubular body 101.

A specific construction of the gateways 102 is not critical so far as it can allow the fluid F to flow into or out from the tubular body when its opened and it can maintain the fluid F immobilized within the tubular body when it is in its closed position.

There may be provided within the tubular body 101 a single sensor employing so-called hot wire method rather than a pair of sensors 150, 151 as in the previously mentioned embodiments so that a temperature of the fluid F is detected by this single sensor before energized for heat generation and then a value of heat generated from the same sensor is detected by this sensor itself as it is energized. Alternately, an arrangement could be adopted such that only the heating sensor 150 is placed within the tubular body 101 and the fluid temperature sensor 151 is placed externally of the tubular body 101.

The configurations of the slits 122, 123, 132, 133 are not limited to those as illustrated in FIGS. 13 and 15. The drive means used to open or close these slits is not limited to the electromotor 107 but may be selected from the other various drive means, for example, those utilizing electromagnet, air pressure, hydraulic pressure, manual mechanism or shape memory alloy. While the movable means to open or close the gateways 102 has been illustrated and described as being provided on the inner tubular element in the above-mentioned embodiments, such means may be provided on the outer tubular element or both the inner and outer tubular elements.

Axis of each sensor may be oriented in any relationship with axis of the tubular body.

The measuring apparatus 10 according to any one of the seventh through eleventh embodiments may be mounted on the fluid tank 16 such as the cell cultivator tank 80 with the measuring apparatus 10 being horizontally oriented relative to the cell cultivator tank 80 as illustrated by FIG. 12A or with the front end of the measuring apparatus 10 being slightly inclined downward relative to the cell cultivator tank 80 as illustrated by FIG. 12B.

The manner in which the measuring apparatus 10 according to any one of the seventh through eleventh embodiments on the fluid tank can be selectively determined depending on a particular situation and, in addition, even when there is a turbulent flow within the fluid tank 16 due to agitation by the agitator, a change in state of the fluid F such as a change in concentration thereof can be reliably detected by the sensors 150, 151 with respect to the quantity of said fluid F maintained immobilized within the tubular body 101.

While the invention has been particularly shown and described with reference to preferred embodiments thereof, it will be understood by those skilled in the art that the foregoing and other changes in for and details can be made therein without departing from the spirit and scope of the invention.

What is claimed is:

1. A method for measuring a change in the state of fluid in a reservoir of subject fluid, comprising:
   (1) placing in the reservoir of subject fluid an apparatus comprising:
      (A) a tubular body having therewithin:
         (i) a fluid inlet;
         (ii) a fluid outlet; and
         (iii) at least one hot wire heating sensor disposed between said inlet and said outlet; and
      (B) a fluid moving means for moving a sample quantity of the fluid from the reservoir into said inlet, through said tubular body and out of said outlet;
   (2) activating said moving means so that a sample quantity of the fluid in the reservoir moves into said tubular body;
   (3) causing said hot wire heating sensor to be heated by said hot wire thereof;
   (4) measuring the temperature of said sensor when said sample quantity of fluid is in a static flow state within said tubular body or in a laminar flow state within said tubular body;
   (5) measuring the temperature of the fluid in the reservoir or the temperature of the sample quantity of the fluid in the tubular body;
   (6) discharging said sample quantity of fluid out of said outlet; and
   (7) determining a change in the state of the fluid based on the measured temperature of the fluid and the measured temperature of the heated sensor.

2. Method for measuring a change in state of a subject fluid as recited in claim 1, wherein, in addition to said heating sensor, a fluid temperature sensor also is disposed within said tubular body to detect the temperature of the fluid.

3. Method for measuring a change in state of a subject fluid as recited in claim 1, wherein the laminar flow state is generated by a fluid impeller means.

4. Method for measuring a change in state of a subject fluid as recited in claim 1, wherein the static flow state is maintained by closing gateways for passage of the fluid into said inlet or out of said outlet.

5. An apparatus for measuring a change in the state of fluid in a reservoir of subject fluid, comprising:
   (1) a reservoir for containing the subject fluid;
   (2) a tubular body having therewithin:
      (i) a fluid inlet;
      (ii) a fluid outlet; and
      (iii) at least one hot wire heating sensor disposed between said inlet and said outlet;
   (3) a fluid moving means for moving a sample quantity of the fluid from the reservoir into said inlet, through said tubular body and out of said outlet;
   (4) control means for causing said hot wire heating sensor to be heated by said hot wire thereof;
   (5) measuring means for measuring the temperature of said sensor when said sample quantity of fluid is in a static flow state within said tubular body or in a laminar flow state within said tubular body;
   (6) measuring means for measuring the temperature of the fluid in the reservoir or the temperature of the sample quantity of the fluid in the tubular body;
   (7) discharging means for discharging said sample quantity of fluid out of said outlet; and
   (8) determining means for determining a change in the state of the fluid based on the measured temperature of the fluid and the measured temperature of the heated sensor.

6. Apparatus for measuring a change in state of a subject fluid as recited in claim 5, wherein a fluid impeller means is provided to generate said laminar flow state.

7. Apparatus for measuring a change in state of a subject fluid as recited in claim 6, wherein said impeller means is an impeller vane assembly having flat vanes adapted to generate a rotational flow around the axis of the tubular body.

8. Apparatus for measuring a change in state of a subject fluid as recited in claim 6, wherein the hot wire heating sensor is oriented to be perpendicular to a direction in which the subject fluid flows.

9. Apparatus for measuring a change in state of a subject fluid as recited in claim 6, wherein the apparatus is incorporated with drive means associated with the impeller vane assembly so as to provide an apparatus which maybe hand held.

10. Apparatus for measuring a change in state of a subject fluid as recited in claim 6, wherein said fluid impeller means comprises a screw-type vane or a propeller vane assembly.

11. Apparatus for measuring a change in state of a subject fluid as recited in claim 10, wherein the heating sensor extends along a direction in which the subject fluid flows.

12. Apparatus for measuring a change in state of a subject fluid as recited in claim 10, wherein there are provided within the tubular body straightening vanes serving to straighten a flow of the subject fluid axially of the tubular body.

13. Apparatus for measuring a change in state of a subject fluid as recited in claim 5, wherein there is provided within the tubular body, in addition to the heating sensor, a fluid temperature sensor used to detect a temperature of the fluid.

14. Apparatus for measuring a change in state of a subject fluid as recited in claim 5, wherein there is provided within the tubular body, in addition to the hot wire heating sensor, a fluid temperature sensor to detect a temperature of the fluid and both these sensors are oriented to extend along a direction in which the fluid flows.

15. Apparatus for measuring a change in state of a subject fluid as recited in claim 5, wherein a fluid impeller means functions to generate a laminar flow state and comprises a screw type vane or a uniaxial eccentric pump.

16. Apparatus for measuring a change in state of a subject fluid as recited in claim 5, wherein a,
   gateway means is provided for passage of the subject fluid into or out from the tubular body, and
   means to open or close said gateway means.

17. Apparatus for measuring a change in state of a subject fluid as recited in claim 16, wherein the tubular body consists of an outer tubular element and an inner tubular element both of which are provided with slits adapted to cooperate mutually to define the gateway means for passage of the fluid into or out from the tubular body.

18. Apparatus for measuring a change of state of a subject fluid as recited in claim 17, wherein any one of said outer and inner tubular elements is axially movable relative to the other in order to open or close the gateway means for passage of the fluid into or out from the tubular body.

19. Apparatus for measuring a change in state of a subject fluid as recited in claim 17, wherein the tubular body comprises a cylindrical structure consisting of an outer cylindrical element and an inner cylindrical element either one of which is rotatable in order to open or close the gateway means for passage of the fluid into or out from the tubular body.

20. Apparatus for measuring a change in state of a subject fluid as recited in claim 16, wherein the wall of the tubular body is partially or entirely movable to provide the gateway means for passage of the fluid into or out from the tubular body.

21. Apparatus for measuring a change in state of a subject fluid as recited in claim 16, wherein the wall of the tubular body is adapted to be axially split to provide the gateway means for passage of the fluid into or out from the tubular body.

22. Apparatus for measuring a change in state of a subject fluid as recited in claim 16, wherein the tubular body comprises a square body and a pair of opposite side walls thereof are rotatable to provide the gateway means for passage of the fluid into or out from the tubular body.

23. Apparatus for measuring a change in state of a subject fluid as recited in claim 16, wherein a temperature of the heating sensor is measured by said heating sensor itself as the sensor is energized for heat generation and the temperature of the fluid is measured by the same heating sensor as the sensor is deenergized and thereby prevented from heat generation.

24. Apparatus for measuring a change in state of a subject fluid as recited in claim 16, wherein there is provided within the tubular body, in addition to the heating sensor, a fluid temperature sensor exclusively used to detect a temperature of the subject fluid.

* * * * *